(12) United States Patent
Frey et al.

(10) Patent No.: US 8,916,035 B2
(45) Date of Patent: Dec. 23, 2014

(54) ARRANGEMENT AND METHOD USING MICROSENSORS FOR MEASURING CELL VITALITIES

(75) Inventors: Alexander Frey, München (DE); Walter Gumbrecht, Herzogenaurach (DE); Peter Paulicka, Röttenbach (DE); Meinrad Schienle, Ottobrunn (DE); Daniel Sickert, Nürnberg (DE); Manfred Stanzel, Berching (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 45 days.

(21) Appl. No.: 13/499,376

(22) PCT Filed: Sep. 29, 2010

(86) PCT No.: PCT/EP2010/064437
§ 371 (c)(1),
(2), (4) Date: Jun. 11, 2012

(87) PCT Pub. No.: WO2011/039242
PCT Pub. Date: Apr. 7, 2011

(65) Prior Publication Data
US 2012/0252055 A1    Oct. 4, 2012

(30) Foreign Application Priority Data

Sep. 30, 2009   (DE) .......................... 10 2009 043 527

(51) Int. Cl.
*G01N 21/41* (2006.01)
*C12M 1/34* (2006.01)
*G01N 27/42* (2006.01)
*G01N 27/416* (2006.01)
*G01N 27/404* (2006.01)

(52) U.S. Cl.
CPC .............. *G01N 27/416* (2013.01); *C12M 41/46* (2013.01); *G01N 27/423* (2013.01); *G01N 27/404* (2013.01); *C12M 41/38* (2013.01)
USPC ... 204/403.01; 204/400; 204/406; 422/82.01; 435/29; 436/149

(58) Field of Classification Search
None
See application file for complete search history.

(56) References Cited

U.S. PATENT DOCUMENTS 5,489,515 A    2/1996   Hatschek et al.
5,563,067 A *  10/1996  Sugihara et al. ........... 435/287.1

(Continued)

FOREIGN PATENT DOCUMENTS

CN    1131744 A    9/1996
DE    4236421      5/1994

(Continued)

OTHER PUBLICATIONS

Schienle et al., A Fully Electronic DNA Sensor with 128 Positions and In-Pixel A/D Conversion, IEEE Journal of Solid-State Circuits, vol. 39, No. 12, pp. 2438-2445, Dec. 12, 2004.*

(Continued)

*Primary Examiner* — Melanie Y Brown
*Assistant Examiner* — Rebecca Martinez
(74) *Attorney, Agent, or Firm* — Roberts Mlotkowski Safran & Cole, P.C.; David S. Safran

(57) ABSTRACT

An arrangement and a method measures cell vitalities with a sensor array. The sensor array is formed on a surface of a semiconductor chip. The semiconductor chip has integrated circuits and an integrated circuit is associated with each sensor of the sensor array, for processing the measurement signals of the respective sensor. The integrated circuits are formed in the semiconductor chip spatially in each case below the associated sensor and neighboring sensors of the sensor array have a center-to-center in the range of micrometers. The pH and/or $pO_2$ can be measured in the environment of a living cell.

17 Claims, 3 Drawing Sheets

(56) References Cited

U.S. PATENT DOCUMENTS

| | | | |
|---|---|---|---|
| 6,277,629 | B1 | 8/2001 | Wolf et al. |
| 6,376,233 | B1 | 4/2002 | Wolf et al. |
| 6,881,379 | B1 | 4/2005 | Bredehorst et al. |
| 7,208,077 | B1 * | 4/2007 | Albers et al. .................. 205/782 |
| 7,809,432 | B2 | 10/2010 | Eversmann et al. |
| 8,128,797 | B2 | 3/2012 | Müller et al. |
| 2002/0119482 | A1 * | 8/2002 | Nelson et al. .................... 435/6 |
| 2002/0123048 | A1 | 9/2002 | Gau |
| 2002/0127733 | A1 * | 9/2002 | Kovacs ......................... 436/149 |
| 2005/0014129 | A1 | 1/2005 | Cliffel et al. |
| 2005/0017190 | A1 * | 1/2005 | Eversmann et al. ..... 250/370.14 |
| 2005/0178700 | A1 | 8/2005 | Tyvoll et al. |
| 2006/0137984 | A1 | 6/2006 | Gumbrecht et al. |
| 2006/0289726 | A1 | 12/2006 | Paulus et al. |
| 2007/0003994 | A1 * | 1/2007 | Simpson et al. ................ 435/25 |
| 2008/0073225 | A1 * | 3/2008 | Paulus .......................... 205/792 |
| 2009/0170212 | A1 * | 7/2009 | Van Der Wijk et al. ...... 436/149 |
| 2011/0121819 | A1 | 5/2011 | Minch et al. |

FOREIGN PATENT DOCUMENTS

| | | |
|---|---|---|
| DE | 19753598 | 7/1999 |
| DE | 19916867 | 10/2000 |
| DE | 102005027245 | 12/2006 |
| DE | 102006033889 | 9/2007 |
| DE | 10 2009 043 527 | 9/2009 |
| JP | 2003-513275 | 4/2003 |
| JP | 2003-532090 | 10/2003 |
| JP | 2006-6281 | 1/2006 |
| JP | 2006-507557 | 3/2006 |
| JP | 2006-510882 | 3/2006 |
| WO | 01/33207 A1 | 5/2001 |
| WO | 2007/084077 A1 | 7/2007 |
| WO | 2008/076406 A2 | 6/2008 |
| WO | 2009/073121 | 6/2009 |
| WO | PCT/EP2010/064437 | 9/2010 |

OTHER PUBLICATIONS

German Office Action for German Priority Application No. 10 2009 043 527.1, issued on Sep. 7, 2010.

PCT/ISA/220, PCT/ISA/210 and PCT/ISA/237 for PCT/EP2010/064437.

U. Frey et al., "Microelectronic system for high-resolution mapping of extracellular electric fields applied to brain slices," Biosensors and Bioelectronics 24 (2009), pp. 2191-2198.

S. Solé et al., "New materials for electrochemical sensing III.Beads," Trends in Analytical Chemistry, vol. 20, No. 2, 2001, pp. 102-110.

International Search Report for PCT/EP2010/064437, mailed on Dec. 28, 2010.

Chinese Office Action mailed Aug. 30, 2013 in corresponding Chinese Application No. 201080043765.3.

Japanese Office Action mailed Oct. 15, 2013 in corresponding Japanese Application No. 2012-531404.

* cited by examiner (State of the art)

ARRANGEMENT AND METHOD USING MICROSENSORS FOR MEASURING CELL VITALITIES

CROSS REFERENCE TO RELATED APPLICATIONS

This application is based on and hereby claims priority to International Application No. PCT/EP2010/064437 filed on Sep. 29, 2010 and German Application No. 10 2009 043 527.1 filed on Sep. 30, 2009, the contents of which are hereby incorporated by reference.

BACKGROUND

In microbiology, a large number of methods are known for the study of pathogenic microorganisms on the basis of cell culture and antibiotic resistance tests. The "phenotypic" approach, in which the action such as for example the growth or the inhibition of cell growth is studied, is advantageous. Via the action on cell cultures, a direct reference to the action on man or animals can be obtained. In this, cell cultures are placed for days on end in a nutrient solution, for example in Petri dishes, and observed. The growth or the damage to the cell cultures is measured and assessed over long periods. The long periods which are necessary for the observation make the method very costly and prolonged.

For the measurement of the growth or the damage to the cell cultures, sensor systems can be used. Living cells are for example grown on sensors in order then to monitor the vitality of the cells for example by measurement of impedance, oxygen ($pO_2$) or pH. As sensors, interdigital electrode arrays, oxygen sensors or pH sensors can be used. Measures of the vitality of the cells are inter alia their adhesion to surfaces, their respiration or their metabolism. However, growing the cells on the sensors is time-consuming and leads to limited storability of the sensor systems. Cells that have grown on the sensors can migrate on the surface and/or die off.

For measurement of the vitality of cells via an oxygen or pH value, it is necessary that living cells be situated in direct proximity to the sensors. Only thus can it be ensured that concentration changes of starting substances or reaction products of the cell metabolism are recorded by the sensors. Here, direct growth of the cells onto the electrodes must be prevented, since for a reliable measurement, for example by electrochemical sensors, a liquid film must be present between cell wall and sensor surface.

Cells have a size in the micrometer range. Normal electrochemical sensors have metal surfaces which are for example made in the form of comb-shaped interpenetrating inter-digital electrodes, with a circular overall sensor perimeter. The diameter of such a sensor as a rule lies in the region of several millimeters. In order to prevent crosstalk of the sensors, the sensors have a distance between one another which likewise lies in the millimeter range. Wall-shaped ridges are often formed between sensors, in order to obtain better separation of the sensors from each other and assignment of signals to regions over the sensors and effectively to suppress crosstalk.

Through their metabolism, individual living cells cause only slight changes in the concentration of chemical and biochemical substances in their vicinity. These slight concentration changes are only measurable if sensors have a high sensitivity for the substance and the cells are arranged close enough to the sensors. Sensors with an overall diameter in the millimeter range can only with difficulty attain a sensitivity that suffices for measuring metabolic products from single cells. Side reactions on large electrode areas lead to poor signal-to-noise ratios. A large distance between the sensors can have the result that cells are located between the sensors and no signals from the cells can be measured.

The distance between the midpoints of two sensors or the highest possible packing density of sensors of a sensor array is also determined by the contacting and arrangement of signal-processing circuits. Thus, with the use of semiconductor supports, integrated circuits can be arranged directly under the sensors. The integrated circuits can be formed for each sensor under the respective sensor, for example with the use of CMOS technology in the silicon support material. The size of a circuit then determines the greatest possible packing density of the respectively assigned sensors of the sensor array lying above it. A common integrated circuit for measuring electro-chemical signals from a sensor has a space usage or an area in the sensor array support which lies in the millimeter range. In particular, the creation of operational amplifiers in integrated circuits leads to a high space usage.

SUMMARY

One potential object is therefore to indicate a device, and a method for measuring cell vitalities using the device, which enable a reliable measurement on living cells with a good signal-to-noise ratio. A further purpose is to indicate a device which ensures that essentially all cells situated on the sensor array can be recorded or measured. A further potential purpose is to indicate a special space-efficient integrated circuit which allows a high packing density of the sensors in the sensor array. Rapid, simple and reliable measurement of parameters which are typical of cell vitality should be enabled thereby.

The inventors propose a device for measuring cell vitalities, which includes a sensor array which is formed on one surface of a semiconductor chip. In this, the semiconductor chip comprises integrated circuits and an integrated circuit is assigned to each sensor of the sensor array for processing the measurement signals of the respective sensor. The integrated circuits in the semiconductor chip are spatially arranged under each assigned sensor. Adjacent sensors of the sensor array have a distance between the midpoints of the adjacent sensors in the micrometer range.

The small size and the small distance of the sensors from each other enables a measurement of slight concentration changes of chemical or biochemical substances in the vicinity of a sensor. Owing to the small area of a sensor, interfering side reactions do not result in a large signal. Spatially very restricted slight concentration changes can thus be reliably recorded and measured.

The distance between the midpoints of adjacent sensors can be of the order of the size of living cells, in particular in the range from 1 to 100 micrometers. Preferably, the distance between the midpoints of adjacent sensors lies in the range from 1 to 10 micrometers, which corresponds to the normal size of a cell. It is thus ensured that all cells situated on the sensor array can be assayed. Cells in the space between two sensors always lie close enough to a sensor for measuring the metabolic products or changes in the concentration of the starting substances for the metabolic products reliably and with a good signal-to-noise ratio.

The sensors can be electrochemical sensors, in particular amperometric or coulometric electrochemical sensors. Electro-chemical sensors can reliably measure concentration changes of chemical or biochemical substances in a very narrow space, even in optically turbid solutions. The magnetic particles lead to no worsening of the signal-to-noise ratio, such as would be the case for example with optical measurements. In contrast to optical measurements, an arrangement of magnetic devices can exert no interfering effect on the arrangement of the electro-chemical measurement device, since electrochemical measurement devices only have to convert, transport and process electrical signals, which is very space-efficient. A pure electrical measurement is less expensive, simpler and more space-efficient than for example optical measurements. The sensors can each comprise at least one interdigital electrode as a working electrode. Interdigital electrodes enable very sensitive electrochemical measurement. Alternatively, the working electrodes can also be formed as a continuous, for example circular, area. Reference and counter-electrodes can be arranged at the border of the sensor array or in the spaces between working electrodes. The arrangement of the reference and counter electrodes at the border of the sensor array allows a smaller distance of adjacent working electrodes of the sensor array from one another and thus enables more reliable measure-ment of all cells situated on the array or of their cell vitality.

The amperometric or coulometric measurements result in a consumption of substances which are also converted by cells. A small active sensor area which lies in the micrometer range ensures that little substance conversion takes place on the electrode. With simultaneous substance conversion by the cell, the substance conversion of the cell can be better measured with a large value for the ratio of substance conversion of the cell to substance conversion of the electrode and the sensor is more sensitive to changes in the vitality of the cells.

In amperometric or coulometric measurements, charge carriers are converted on the sensors in chemical reactions, and then serve as the measurement signal. With low concentrations to be measured of substances which are converted by the cells, only small quantities of charge carriers are converted on the sensors and thus only small measurement signals are created. In order to be able to process these, conduction paths must be kept short, since electrical losses in the paths lead to a loss of signal. As a rule, therefore, the signals of the sensors are directly amplified or processed close to a sensor. For this, integrated circuits are arranged in the semiconductor material directly under a sensor. Electrical components of integrated circuits, such as for example operational amplifiers or condensers, lead to a high area usage in the semiconductor material. In order to make smaller sensors possible, which are arranged closely packed on a surface in array form, integrated circuits which are each of the same order of size as a sensor must be arranged under the sensors.

The integrated circuit of a sensor can comprise two switching transistors for switching the sensor, in particular the working electrode of the sensor in question. Here, the transistors can enable switching of the potential present on the working electrode between two potential values, a first and a second potential. Integrated circuits without components such as for example operational amplifiers or condensers, mainly or exclusively comprising transistors, result in a low area usage of an integrated circuit in the semiconductor material. As a result, a dense packing of the small sensors arranged over the integrated circuits becomes possible.

The integrated circuit of a sensor can comprise a transistor as voltage follower and a selection transistor, for specific electrical selection of the respective sensor by column and row of the sensor array. The transistors, in particular made using CMOS technology, require little space in the semiconductor material. Each sensor of the sensor array can be individually selected and read off. The electrical measurement itself is effected by the switching of the switching transistors from the first to the second potential. Via the transistor as voltage follower and the selection transistor, one sensor is read off each time.

To suppress electrical noise signals and to suppress electrical drift of a sensor, the integrated whole circuit can comprise for each sensor a correlated double sampling stage (CDS), which is arranged below the assigned sensor or in a region of the semiconductor chip outside the region of the sensor array. The arrangement of the double sampling stages (CDS) in a region of the semiconductor chip outside the region of the sensor array leads to a particularly high integration density of the integrated circuits under the sensors.

The device can further comprise a device for setting a defined temperature over the sensor array. In particular, a temperature of 37° C. is favorable for the vitality of the cells. Setting and maintaining this temperature constant over the whole measurement time enables a comparison of different measurements or yields comparable conditions throughout the whole measurement time.

The device can comprise a device for immobilizing living cells over sensors of the sensor array. Freely mobile cells can migrate on a surface, which can interfere with an electrochemical measurement. Particularly with regard to monitoring of measured values over longer time periods, migration of cells on the sensor array must be prevented.

For this, a filter membrane which is arranged in fluid contact with the sensors of the sensor array can serve as the device for the immobilization of living cells. By exchange of the filter membrane, dead cells can be removed after a measurement and the device for measuring cell vitalities regenerated for a further measurement or be prepared by laying a new filter membrane with fresh, living cells onto the sensor array.

Alternatively, the device can comprise at least one device creating a magnetic field, which is configured to create a magnetic field over the sensors of the sensor array. Living cells can be bound to magnetic particles and immobilized over the sensor array by the magnetic field. Here it is particularly favorable for a measurement if this is effected in the form of an essentially uniformly thick layer which is composed of magnetic particles with cells embedded in the matrix of magnetic particles.

The magnetic field can be switchable between an on and an off state. Thereby, dead or damaged cells can be removed in the switched-off state of the magnetic field, e.g. by a liquid flow.

The semiconductor chip can be surrounded by a flow cell and the sensors of the sensor array can be arranged in fluid contact with a flow channel of the flow cell. This gives an especially simple measurement configuration for the device for measuring cell vitalities.

The inventors also propose a method for measuring cell vitalities with use of the previously described device comprises the measurement of the pH and/or the $pO_2$ in the vicinity of a living cell by at least one sensor of the sensor array. Alternatively, proteins can also be measured. These substances are starting materials or reaction products of the cell metabolism. The measurement of the slight changes in the substance concentrations caused by a cell is only made possible by the small size and the close packing of the sensors in the sensor array. Because the distance between the midpoints of two adjacent sensors is in the micrometer range, consumption of for example oxygen is so greatly reduced that the small consumption of for example oxygen by a cell in the vicinity of the sensor can be measured.

It is advantageous here if a temperature optimal for cell vitality is set over the sensor array, in particular in the region of 37° C., and/or substances are supplied to the cells which favor or maintain cell vitality, in particular nutrient solution and/or oxygen, and/or substances are supplied to the cells which impair cell vitality, in particular antibiotics.

The advantages connected with the method for measuring cell vitalities using the device are analogous to the advantages which were previously described with reference to the device for measuring cell vitalities.

BRIEF DESCRIPTION OF THE DRAWINGS

These and other objects and advantages of the present invention will become more apparent and more readily appreciated from the following description of the preferred embodiments, taken in conjunction with the accompanying drawings of which.

DETAILED DESCRIPTION OF THE PREFERRED EMBODIMENT

Figure 1:
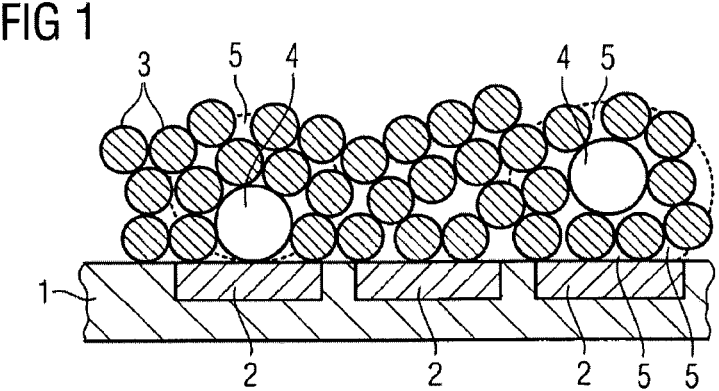
FIG. 1 shows a schematic cross-sectional representation through a semiconductor chip with sensors of a sensor array and layer situated thereon, of magnetic particles with embedded cells.

Reference will now be made in detail to the preferred embodiments of the present invention, examples of which are illustrated in the accompanying drawings, wherein like reference numerals refer to like elements throughout.

FIG. 1 shows a device of cells 4 arranged in a matrix of magnetic particles 3 on sensors 2 of a sensor array in a cross-sectional representation. The sensor array is formed on a semiconductor chip 1, which comprises integrated circuits for the electrochemical measurement by the sensors 2. The magnetic particles 3 are magnetically immobilized on the surface of the chip 1 in the form of a layer of essentially uniform thickness by a magnetic field-creating device, not shown. The cells 4 can be bound onto the magnetic particles 3, e.g. by antibodies, or be grown onto the particles. The magnetic particles 3 have a size in the micrometer or nanometer range, and the cells have a size in the range of a few micrometers. With living cells, metabolic products can be measured in the direct vicinity 5 of the cells 4, as can the consumption of substances necessary for the metabolism such as for example oxygen.

The sensors 2 for the electrochemical measurement of the metabolic products and/or starting materials for the metabolic products are composed of a metal, e.g. gold. A thin gold layer is applied onto the chip 1 as a support material, wherein for example intermediate layers can serve as adhesion promoters between gold layer and support material. The sensors 2 made for example of the gold layer are formed in circular shape with a midpoint which corresponds to the circle center. The circular sensors 2 are arranged in columns and rows as an array on the chip surface, wherein the midpoints of the sensors 2 are each arranged at the intersection points of the rows and columns of the array. The support material is formed from a semiconductor material such as for example silicon, wherein integrated circuits for selection and processing of the electrochemical signals measured on the sensors 2 are formed in the material. The circuit can be created in the semiconductor material for example by CMOS technology.

Figure 2:
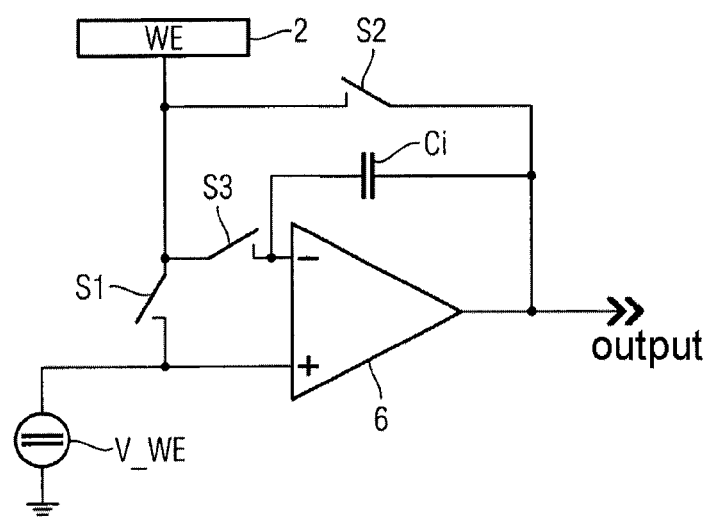
FIG. 2 shows a schematic representation of an integrated circuit for electrochemical measurement with a sensor according to the related art.

FIG. 2 shows a circuit for selection and electrochemical measurement with a sensor such as is known from the related art. For simplicity, the reference electrode and counter electrode are not shown. The working electrode WE constitutes the sensor 2 and can be made in circular shape or as an interdigital electrode. In a practical example, oxygen can be measured in the form of the $pO_2$ in a liquid by the sensor array composed of sensors 2 arranged in rows and columns on the chip surface. The $pO_2$ is a measure of the vitality of living cells 4 which are situated close to a sensor 2. In its metabolism, a living cell 4 consumes oxygen and the decrease in the oxygen in its vicinity can be measured.

For this, the array surface is supplied with air-saturated nutrient solution. The liquid flow is stopped for a brief time and the oxygen concentration in the form of the $pO_2$ is measured via the sensors 2. The $pO_2$ values remain constant unless an oxygen consumer in the form of a living cell 4 causes the $pO_2$ to fall locally. This is recorded by the nearest sensor 2, under the precondition of little or no oxygen consumption by the sensor 2 during the measurement compared to the oxygen consumption of the cell 4 and under the precondition of a small distance between cell 4 and sensor 2. The position of the living cell 4 can be concluded from the position of the sensor 2 in the sensor array. The living cells 4 on the sensor array are thus spatially identified.

Next, a flow of nutrient solution treated with antibiotics is passed over the sensor array and the liquid flow is stopped. If the previously spatially identified cells 4 are each sensitive to the antibiotic in question, then no fall in $pO_2$ is measured at the relevant nearest sensor 2. Furthermore, at sensor positions at which living cells 4 are arranged, which are not sensitive to the antibiotic in question, a decrease in the $pO_2$ corresponding to the cell metabolism is measured.

In order to prevent or reduce falsification of the measured $pO_2$ values due to oxygen consumption of the sensors 2 themselves in amperometric or coulometric measurements, a pulse method can be used. In electrochemistry, the oxygen partial pressure is typically measured with an amperometric method, i.e. a Faraday current is used as a measure of the oxygen concentration, which in coulometric measurement is integrated over time. During this, oxygen is converted at the electrode or at the sensor 2 and is thus consumed. This leads to a change in the oxygen concentration and thus to a falsification of the measured value of the oxygen consumption by the cell 4. By use of short measurement times, i.e. a pulse method, this effect can be reduced. The sensors 2 are only cathodically polarized briefly for the measurement.

With excessively short pulses, however, the polarization leads to a current flow due to charge reversal of the liquid or electrolyte double layer capacity via the sensor 2. The process is completed rapidly, so that only a brief current flow takes place. Here, the current flow is dependent on the area of the sensor 2. The smaller the electrochemically active area of the sensor 2 is, the smaller the interfering effect due to the charge reversal of the double layer becomes and the more rapidly the current flow caused by charge reversal of the double layer is completed. After the capacitive current flow due to charge reversal of the double layer has subsided, the current flow arising can be used as a measure of the oxygen partial pressure. Next, the sensor 2 or the electrode is switched to resting potential in order to avoid further oxygen conversion by the electrode.

Alternatively to the cathodic polarization of the sensor 2, a recycling of the reaction products, such as for example $H_2O_2$ to oxygen, can be effected by brief anodic polarization of the sensor 2. Instead of a resting potential, a suitable anodic polarization of the sensor 2 can also be effected, in order to recover at least a part of the converted oxygen.

Through the embedding of the cells 4 in a "lattice" or a matrix of magnetic particles or magnetic beads 3, as shown in FIG. 1, defined liquid spaces are created between the particles 3 or the cells 4 and the sensor 2. With a thickness of the layer of magnetic particles 3 with embedded cells 4 which lies in the region 5 of the change in the measured quantity which is created by the metabolism of a cell 4, a sensitive electrochemical detection of the vitality of the cell is ensured. By narrowing the liquid spaces in the vicinity of the cells 4 by the magnetic particles 3, the sensitivity of the measurement is increased compared to cells 4 present free in liquid without magnetic particles 3.

Alternatively to the $pO_2$, metabolic products of the cell such as acids can be measured via the pH. Analogously to the $pO_2$, the smaller the liquid volume surrounding the cells 4 is, the greater the pH change.

The amperometric signal of a sensor 2 can be converted into a voltage signal by the circuit according to the related art shown in FIG. 2. The integrator circuit integrates the current in a defined time interval after the pulsed application of the polarization on a sensor 2 and converts the result into a voltage.

Figure 3:
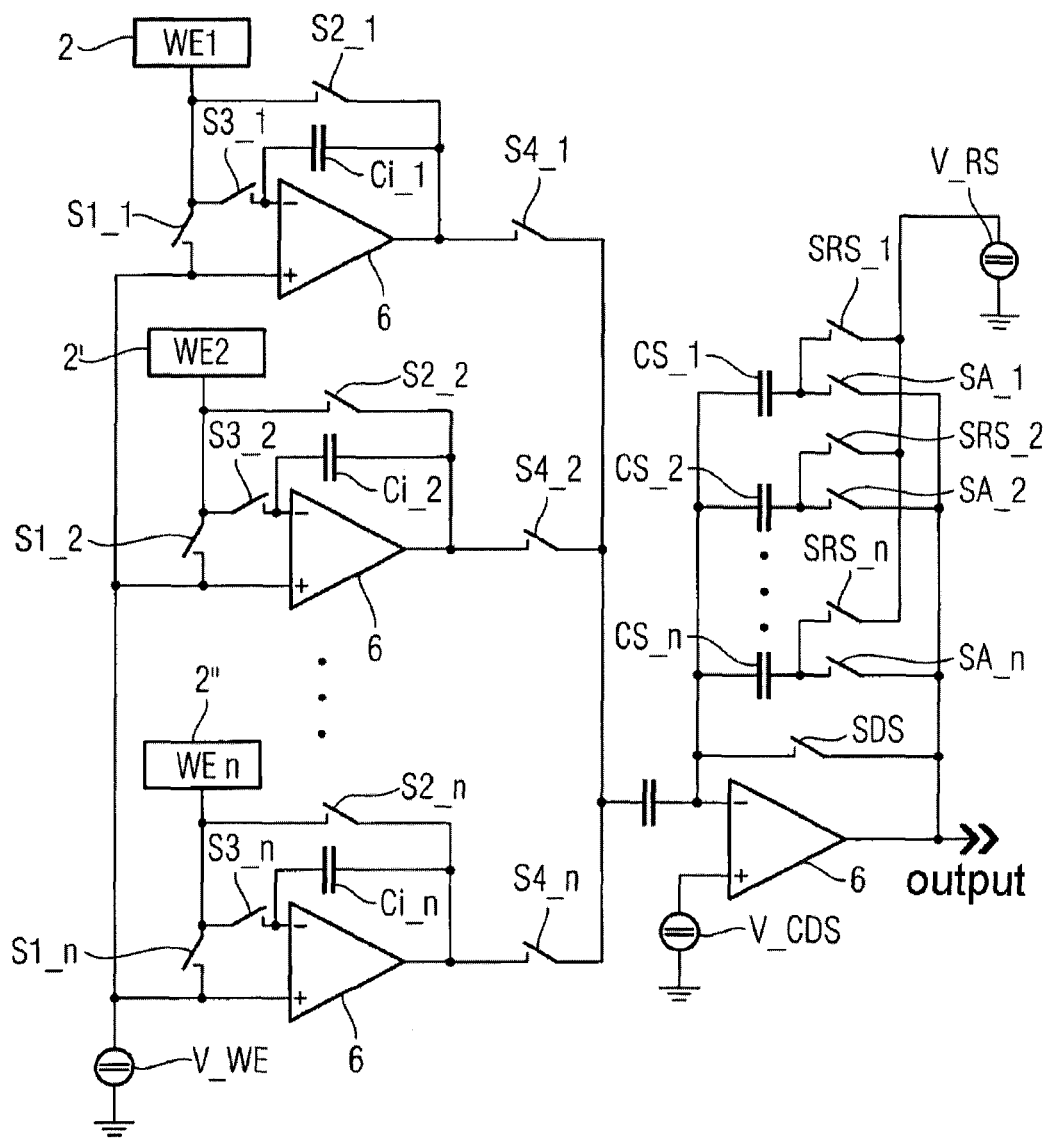
FIG. 3 shows a schematic representation of an integrated circuit for electrochemical measurement with a sensor array with the use of a CDS stage.

To suppress offset signals, a double sampling stage or a correlated double sampling stage (CDS), as shown in FIG. 3, can be used. In this, the zero point effect is detected in close time correlation with the measurement signal. This can be effected directly before or after the determination of the measurement signal. All drifts and noise components which arise before the CDS stage are thereby effectively suppressed. In a sensor array, not every sensor 2 necessarily requires its own CDS stage. Rather, the CDS stages can be arranged in a border region of the chip 1 outside the sensor array area. Each stage is then for example assigned to one column of the sensor array.

Figure 4:
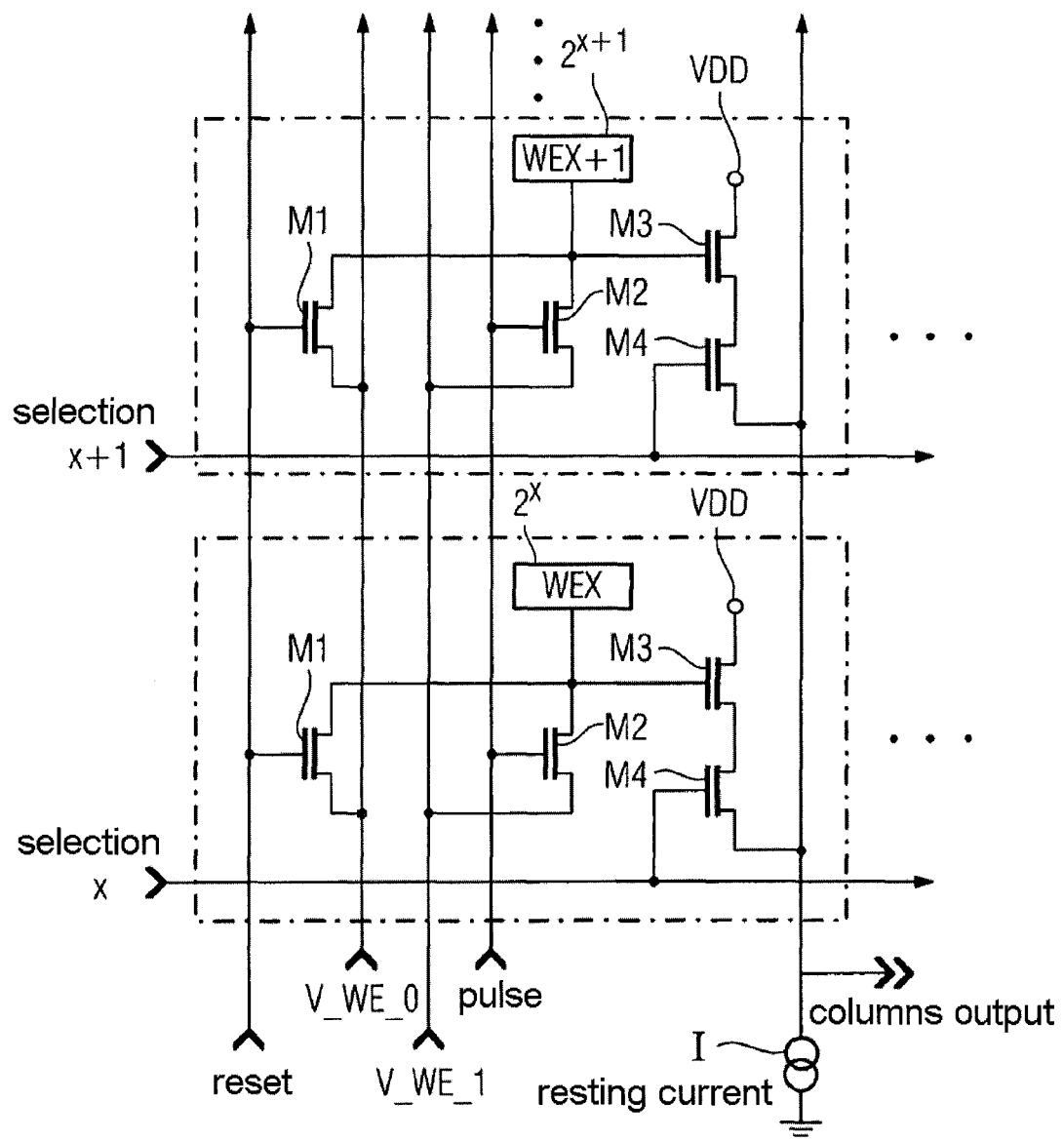
FIG. 4 shows a schematic representation of a proposed space-efficient integrated circuit for electrochemical measurement with sensors of a sensor array made up exclusively of transistors.

One configuration of an integrated circuit for measurement with a sensor array is shown in FIG. 4. Here, the CDS stages are arranged at the border of the semiconductor chip 1 and for simplicity are not shown in FIG. 4. The CDS stages can also possibly be dispensed with.

In the integrated circuit shown in FIG. 4, the voltage on the sensors 2 or working electrodes $WE_x$ is not regulated by an amplifier 6, as is the case in FIG. 2, but rather the sensors 2 or working electrodes $WE_x$ are connected with the desired voltages V_WE_0 and V_WE_1 directly by circuits. Thereby, sensor circuits with a minimal requirement of components such as for example transistors and of chip area or chip surface become possible. The sensors 2 arranged over the respective integrated circuit can be arranged with a higher integration density compared to the related art, and thus smaller sensor areas and/or smaller sensor spacings can be selected in order to build the sensor array. This has the previously described advantages, i.e. no cells 4 can be located between sensors 2 in the magnetic particle matrix the vitality whereof cannot be measured by sensors 2 or the substance conversion whereof cannot be measured, subject to the precondition of a small layer thickness. The smaller electrochemically active sensor surfaces give a sensitive measurement for example of oxygen conversion or other quantities influenced by the cell metabolism, with only little or no interfering substance conversion on the sensors 2 themselves.

The integrated circuit represented in FIG. 4 manages with only four transistors M1 to M4 per sensor 2 or electrode $WE_x$. The transistors M1 and M2 serve as switching transistors or switches, through which the working electrode $WE_x$ of the sensor $2^x$ respectively is optionally supplied with the voltage V_WE_0 or V WE_1. X in this case stands for the row of the sensor $2^x$ to be selected. At the start of a measurement with a sensor $2^x$, the electrode $WE_x$ or the electrochemically active area of the sensor $2^x$ is connected with the voltage V_WE_0 by closing of the switch M1. The voltage V_WE_O is selected such that no electrochemical reaction of the measurement quantity typical of the cell vitality takes place at the working electrode $WE_x$. Then, the switch M1 is opened and by closing of the switch M2 the electrode $WE_x$ is brought to a voltage V_WE_1. Next, the switch M2 is opened again. Through the electrochemical reaction, the electrode $WE_x$ discharges with a time constant which is determined by the double layer capacity and the electrochemical current. After a defined time, the voltage of the electrode $WE_x$ is read off via the transistors M3 and M4. M3 functions here as a voltage follower and M4 is the selection transistor via which the sensor 2 with the position X in the sensor array is selected and connected with the exit Column Out. The voltage read off then is available at the exit Column Out for further processing. For zero point suppression, the CDS stage of FIG. 3 can also be connected at the exit Column Out.

With the circuit from FIG. 4, sensor arrays can be created which have a distance between the midpoints of adjacent sensors $2^x$ and $2^{x+1}$ or array grids of down to 10 μm. Electrical components, such as for example operational amplifiers 6 or condensers Ci do not have to be created in the integrated circuit directly under a respective sensor 2, as a result of which a high integration density of the circuit directly under a sensor 2 is achieved. Integrated circuits which enable further signal processing can be contained on the chip 1, e.g. in the border region. Integrated circuits such as for example potentiostats or integrated circuits for current measurement can be arranged on the chip 1 outside the region of the sensor array.

The device and the method for measuring cell vitalities can be used in environmental and pharmaceutical studies, for example in order to identify toxic substances. Thus for example pollutants in water or air can be studied or the action of drugs on for example tumor cells can be studied. In this, a defined number of living cells can be fed into the sensor array and damaged or dead cells can be removed again after a measurement. Further measurements can then subsequently be made by introduction of fresh living cells.

The device and the method for measuring cell vitalities can however also be used in health examinations. In this case, an identification of an undetermined number of cells such as for example *Staphylococcus aureus* bacteria can be effected analogously to a microbiological detection on nutrient media. Because of the more sensitive measurement technique, this identification can be effected much more quickly than the time-consuming detections by growing the cell cultures until they are optically visible under an optical microscope. Through the use of sensor arrays with a high sensor packing density, in the same way as in Petri dishes, local microorganisms can be identified with high spatial resolution via the colonies arising from them, purely via the cells of the microorganisms. Antibiotic resistance tests, e.g. for the detection of MRSA, can be performed on the microorganisms by introduction of increasing concentrations of defined antibiotics and measurement of the cell vitality.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide v. DIRECTV*, 69 USPQ2d 1865 (Fed. Cir. 2004).

The invention claimed is:

1. A device to measure cell vitalities, comprising:
    a semiconductor chip;
    a sensor array formed on one surface of the semiconductor chip, the sensor array comprising a plurality of sensors, each sensor producing a measurement signal and comprising a working electrode, the sensor array being arranged such that midpoints of adjacent sensors are separated by a distance of from 1 to 999 micrometer; and
    integrated circuits formed in the semiconductor chip such that an integrated circuit is assigned to each sensor of the sensor array to process the measurement signal produced by the assigned sensor, the integrated circuits in the semiconductor chip are each spatially formed under the sensor assigned thereto, and each integrated circuit comprises
        a first switching transistor which supplies the working electrode of the assigned sensor with a first voltage when the first switching transistor is closed,
        a second switching transistor which supplies the working electrode of the assigned sensor with a second voltage, different from the first voltage, when the second switching transistor is closed,
        a voltage follower transistor that provides a third voltage that follows a voltage supplied to the voltage follower transistor by the working electrode of the assigned sensor, and
        a selection transistor which, together with the voltage follower transistor, electrically selects the assigned sensor by a column and a row of the sensor array.

2. The device as claimed in claim 1, wherein the midpoints of adjacent sensors are separated by a distance in a range of from 1 to 100 micrometers.

3. The device as claimed in claim 1, wherein the midpoints of adjacent sensors are separated by a distance in a range of from 1 to 10 micrometers.

4. The device as claimed in claim 1, wherein
    the sensors are amperometric or coulometric electrochemical sensors, and/or
    the sensors each comprise at least one interdigital electrode as a working electrode.

5. The device as claimed in claim 1, wherein each integrated circuit comprises a correlated double sampling stage (CDS) to suppress electrical noise signals and suppress electrical drift of the assigned sensor, and the correlated double sampling stage (CDS) is arranged under the assigned sensor or in a region of the semiconductor chip outside of the sensor array.

6. The device as claimed in claim 1, further comprising a temperature controller to set a defined temperature over the sensor array.

7. The device as claimed in claim 1, wherein further comprising means for immobilizing living cells over the sensors of the sensor array.

8. The device as claimed in claim 7, wherein the means for immobilizing living cells comprises a filter membrane arranged in fluid contact with the sensors.

9. The device as claimed in claim 7, wherein
    the means for immobilizing living cells comprises a magnetic field-creating device, which is configured to create a magnetic field over the sensors of the sensor array, and the living cells are bound to magnetic particles.

10. The device as claimed in claim 9, wherein the magnetic field-creating device immobilizes the living cells over the sensor array in the form of an essentially uniformly thick matrix of magnetic particles with the living cells embedded in the matrix of magnetic particles.

11. The device as claimed in claim 10, wherein
    the magnetic field is switchable between an on state and an off state, and
    dead or damaged cells are removed in the off state of the magnetic field.

12. The device as claimed in claim 1, wherein
    the semiconductor chip is surrounded by a flow cell, and
    the sensors of the sensor array are arranged in fluid contact with a flow channel of the flow cell.

13. A method for measuring cell vitalities, comprising:
    providing a device comprising:
        a semiconductor chip;
        a sensor array formed on one surface of the semiconductor chip, the sensor array comprising a plurality of sensors, each sensor producing a measurement signal and comprising a working electrode, the sensor array being arranged such that midpoints of adjacent sensors are separated by a distance of from 1 to 999 micrometer; and
        integrated circuits formed in the semiconductor chip such that an integrated circuit is assigned to each sensor of the sensor array to process the measurement signal produced by the assigned sensor, the integrated circuits in the semiconductor chip are each spatially formed under the sensor assigned thereto, and each integrated circuit comprises
            a first switching transistor which supplies the working electrode of the assigned sensor with a first voltage when the first switching transistor is closed,
            a second switching transistor which supplies the working electrode of the assigned sensor with a second voltage, different from the first voltage, when the second switching transistor is closed,
            a voltage follower transistor that provides a third voltage that follows a voltage supplied to the voltage follower transistor by the working electrode of the assigned sensor, and
            a selection transistor which, together with the voltage follower transistor, electrically selects the assigned sensor by a column and a row of the sensor array;
    bringing living cells into contact with the sensors; and
    measuring pH and/or the $pO_2$ in a vicinity of the living cells using the sensors of the sensor array.

14. The method as claimed in claim 13, further comprising:
    setting a temperature over the sensor array to 37° C. or a different temperature optimal for cell vitality; and/or
    supplying nutrients and/or oxygen to the cells which favor cell vitality; and/or
    supplying antibiotics or other substances to the cells to impair cell vitality.

15. The device as claimed in claim 1, wherein the voltage follower transistor has a gate terminal electrically connected to the working electrode.

16. The device as claimed in claim 1, wherein when the selection transistor is closed, the third voltage is supplied through the selection transistor.

17. The device as claimed in claim 1, wherein the second switching transistor supplies the working electrode of the assigned sensor with the second voltage when the second transistor is closed while the first switching transistor is open.

* * * * *